(12) United States Patent
Zeng et al.

(10) Patent No.: US 12,616,652 B2
(45) Date of Patent: May 5, 2026

(54) LENSES FOR TREATING OCULAR DISEASES AND PREPARATION METHOD THEREOF

(71) Applicant: Guangdong ProCapZoom Biosciences Co., Ltd., Guangzhou (CN)

(72) Inventors: Haoyu Zeng, Guangzhou (CN); Zhenbo Shen, Guangzhou (CN); Yuanyue Liu, Guangzhou (CN); Tian Guan, Guangzhou (CN); Jiexing Chen, Guangzhou (CN)

(73) Assignee: Guangdong ProCapZoom Biosciences Co., Ltd., Guangzhou (CN)

( * ) Notice: Subject to any disclaimer, the term of this patent is extended or adjusted under 35 U.S.C. 154(b) by 546 days.

(21) Appl. No.: 18/148,421

(22) Filed: Dec. 29, 2022

(65) Prior Publication Data

US 2024/0216269 A1 Jul. 4, 2024

(51) Int. Cl.

| | |
|---|---|
| *A61K 9/00* | (2006.01) |
| *A61K 35/28* | (2015.01) |
| *A61K 41/17* | (2020.01) |
| *A61K 47/34* | (2017.01) |
| *A61P 27/02* | (2006.01) |
| *A61P 37/06* | (2006.01) |
| *C12N 5/0775* | (2010.01) |

(52) U.S. Cl.
CPC ............ *A61K 9/0051* (2013.01); *A61K 35/28* (2013.01); *A61K 41/17* (2020.01); *A61K 47/34* (2013.01); *A61P 27/02* (2018.01); *A61P 37/06* (2018.01); *C12N 5/0665* (2013.01)

(58) Field of Classification Search
CPC ...... A61K 9/0051; A61K 41/17; A61K 35/28; A61K 47/34; A61P 27/02; A61P 37/06; C12N 5/0665
See application file for complete search history.

(56) References Cited

U.S. PATENT DOCUMENTS

| | | | | |
|---|---|---|---|---|
| 9,682,160 | B2 * | 6/2017 | Tseng ..................... | A61L 2/0035 |
| 2007/0291223 | A1 * | 12/2007 | Chen ..................... | G02B 1/043 |
| | | | | 351/159.02 |
| 2015/0368386 | A1 * | 12/2015 | Nicholson ............. | C08F 230/08 |
| | | | | 526/264 |
| 2016/0030480 | A1 * | 2/2016 | Mistry ................... | A61K 45/06 |
| | | | | 424/93.7 |

* cited by examiner

*Primary Examiner* — Zohreh A Fay

(57) ABSTRACT

The disclosure provides lenses for treating ocular diseases, including a bowl-shaped silicone hydrogel carrier and umbilical cord mesenchymal stem cells loaded on the carrier; the bowl-shaped silicone hydrogel carrier is polymerized from an organosilicone monomer and a hydrophilic monomer under the action of a cross-linking agent and an initiator; the organosilicone monomer is polymerized from a hydrogenated silicone oil and allyl methacrylate under the action of a polymerization inhibitor and a catalyst; and the umbilical cord mesenchymal stem cells are treated with irradiation.

15 Claims, 14 Drawing Sheets

|  | Before | After |
|---|---|---|
| OD | | |
| OS | | |

Vision: 1.0 (OD);1.1 (OS)
Intraocular pressure:13 mmHg (OD);
16 mmHg (OS)
Area of corneal ulcer:
21.83 mm²(OD);25.58 mm²(OS)

Vision: 0.9 (OD);1.1 (OS)
Intraocular pressure:13 mmHg (OD);
15 mmHg (OS)
Area of corneal ulcer:
16.43 mm²(OD);16.19 mm²(OS)

Vision:  1.1  (OD);0.9 (OS)      Vision:  1.1  (OD);0.9(OS)
Intraocular pressure:18 mmHg (OD);  Intraocular pressure:18 mmHg(OD);
14 mmHg (OS)              13 mmHg(OS)
Area of corneal ulcer:        Area of corneal ulcer:
24.64 mm²(OD);20.18 mm²(OS)    2.35 mm²(OD);6.81 mm²(OS)

Before

After

OD

Vision: 0.25
Intraocular pressure:16 mmHg;
Area of corneal ulcer: 23.13 mm$^2$

Vision: 0.4
Intraocular pressure:14 mmHg;
Area of corneal ulcer: 21.05 mm$^2$

LENSES FOR TREATING OCULAR DISEASES AND PREPARATION METHOD THEREOF

FIELD

The present disclosure belongs to the field of biotechnology, in particular to lenses for treating ocular diseases and a preparation method thereof.

BACKGROUND

Chronic ocular graft-versus-host disease (oGVHD) is caused by allogeneic hematopoietic stem cell transplantation (allo-HSCT), results from an imbalance in the protective immune mechanism and inflammatory mechanism of the ocular surface, which is essentially that donor's T cells attack recipient's eye tissues including the fibroblasts of the recipient's lacrimal duct, which makes the lacrimal duct fibrotic, severely affecting the secretory function of the lacrimal gland. The clinical manifestations of oGVHD are mainly ocular surface inflammation, dry eye and corneal ulcer, which in severe cases can lead to a series of complications threatening visual function and ocular health, such as corneal perforation and atretoblepharia. Thus, oGVHD severely affects the vision and the quality of life of a patient, and often results in vision loss of the patient if not diagnosed early and properly treated. A strategy to treat oGVHD is to prevent overactive donor's T cells from attacking recipient's lacrimal duct and other eye tissues.

There is no specific drug for the treatment of oGVHD at current. The three drugs (imbruvica, belumosudil and ruxolitinib) approved by FDA to treat chronic graft-versus-host disease are not targeted at oGVHD and cannot alleviate the symptoms of oGVHD. Current treatment solutions for oGVHD include systemic administrations, topical treatments, and surgical treatments. The systemic administrations commonly use steroid hormones or combined calcineurin inhibitors/immunosuppressants (e.g., cyclosporine and tacrolimus), but systemic administration is difficult to achieve effective drug concentrations in the eye, has negative impact on the therapeutic effect of allo-HSCT, and easily causes infection. The topical treatments mainly include artificial tears (limitations: corneal calcification caused by long-term use), ophthalmic lubricants (limitations: existence of preservatives, which in turn cause additional problems), topical immunosuppressants (limitations: incapability of reversing the damage that has occurred), autologous serum eye drops (limitations: high cost, difficulty in preservation, and easiness in contamination), lacrimal punctum embolism (disadvantages: prolong the time that inflammatory factors remain in the tears to worsen the disease course), and wearing contact lenses (disadvantages: aggravation of local inflammation in the absence of tears). For severe cases, tarsorrhaphy may be performed (shortcomings: incapability of excluding intraocular secretions normally to result in ocular infections). The above three solutions cannot prevent/repair corneal scarring and have limited application and efficacy. Therefore, the key to treat oGVHD is local prevention of attack of hyperactive donor's T cells on recipient's lacrimal duct and other eye tissues.

Umbilical Cord Mesenchymal Stem Cells (UCMSCs) have unique immunomodulatory effects: by secreting soluble cytokines, regulating the release of multiple anti-inflammatory factors, inhibiting the proliferative response of T cells when T cells are stimulated by alloantigens, thereby allowing the body to acquire immunological tolerance, and maintaining immunological homeostasis. Indoleamine 2,3-dioxygenase (IDO) secreted by UCMSCs play a major role in inhibiting the proliferative response of T cells by UCMSCs: by stimulation of interferon γ (IFN-γ), UCMSCs secrete IDO that degrades tryptophan to produce kynurenine, which in turn inhibits proliferation of T cells and promotes the apoptosis of T cells. UCMSCs can also promote the proliferation and activation of regulatory T cell (Treg cells) and inhibit the proliferation and activation of a subset of pro-inflammatory T helper cells (including Th1 and Th17 cells) so as to inhibit expressions of pro-inflammatory cytokines TNF-α, IFN-γ. IL-6, and IL-23, and can promotes expression of the anti-inflammatory factors IL-4, and inhibits expressions of the metalloproteinases MMP1, MMP2 and MMP9, so as to reduce inflammatory damage in the body and maintain self-tolerance of the body, and promote the body to switch from an inflammatory environment to an anti-inflammatory environment to induce immunological tolerance. Thus, the immunomodulatory role of UCMSCs offers the potential for their use in the clinical treatment of oGVHD.

UCMSCs are used in a variety of methods internally, externally, systemically, and topically. oGVHD requires a topically external treatment method because intravenous or local injection of UCMSC into the body interferes with or affects the therapeutic effect of allo-HSCT. Whereas topically external UCMSCs can only inhibit the attack of donor's T cells on recipient's lacrimal duct and other eye tissues at the ocular surface without affecting the normal function of the donor's T cells as desired elsewhere in the body.

However, the biggest hurdle at present is the inability of long-term retention of UCMSCs on the ocular surface.

SUMMARY

The objective of the present disclosure is to provide lenses that can stay on the ocular surface for a long time for the treatment of a variety of ocular diseases including oGVHD.

Lenses for treating ocular diseases, comprising a bowl-shaped silicone hydrogel carrier and umbilical cord mesenchymal stem cells (UCMSCs)

UCMSCs loaded on the carrier; the bowl-shaped silicone hydrogel carrier is polymerized from an organosilicone monomer and a hydrophilic monomer under the action of a cross-linking agent and an initiator; the organosilicone monomer is polymerized from a hydrogenated silicone oil and allyl methacrylate under the action of a polymerization inhibitor and a catalyst; and the UCMSCs are treated with irradiation.

The Lenses for treating ocular diseases of the present disclosure are composed of UCMSCs that do not proliferate after irradiation, and the silicone hydrogel carrier, which are referred to as Mesenchymal Stem Cell-coating High Oxygen Permeable Hydrogel Lenses (MSCohi-O lenses). Each MSCohi-O lens is loaded with $1.0\text{--}2.0\times10^5$ UCMSCs irradiated with 15 Gy (irradiated UCMSCs have no proliferative ability after irradiation, which is more convenient to maintain a steady state for local administration, thereby avoiding affecting the therapeutic effect due to cell shedding). Administration by a topically external method not only allows the UCMSCs to accurately reach and stay at a target organ, but also reduces the safety risk. UCMSCs loaded on MSCohi-O lenses treat oGVHD by: 1) promoting proliferation and activation of Treg cells; 2) inhibiting proliferation of Th1 and Th17 cells; 3) secreting IDO to locally inhibit proliferation of donor's T cells in the eye; and 4) inhibiting the secretion of inflammatory factors and growth factors by T cells, and promoting the secretion of anti-inflammatory factors by T cells to jointly inhibit the attack of donor's T cells on recipient's lacrimal duct and other eye tissues. Compared to blood vessels at other sites, the special blood-ocular barrier structure of the eye limits the entry of blood-borne cells and molecules into the microvessels of ocular tissues. Thus, UCMSCs that are loaded on MSCohi-O lenses and no longer proliferate after irradiation have a minimal probability of entering the systemic circulatory system by accidental shedding and crossing the blood-ocular barrier. Therefore, MSCohi-O lenses do not interfere with or affect the therapeutic effect of allo-HSCT while treating oGVHD on the ocular surface.

For the topically external method of administration to the eye, the characteristics of no proliferation ability of UCMSCs after irradiation, and the special blood-ocular barrier structure of the eye ensure the safety of MSCohi-O lenses while treating oGVHD.

Silicone hydrogel is a hydrophilic organic polymer material with bulky silicone oxygen groups. Organosilicone is a substance with better oxygen permeability, and thus, the silicone hydrogel has both the high oxygen permeability of organosilicone materials and the soft and hydrophilic characteristics of hydrogel materials, which can transport oxygen through two channels (an organosilicone phase and a hydrogel phase), and has a "honeycomb" structure. In addition, the addition of the organosilicone also plays the role of enhancing the mechanical properties of the materials.

MSCohi-O lenses prepared by loading UCMSCs onto the silicone hydrogel can be physiologically compatible with the human eyes after being placed into the eyes.

The present disclosure further provides a preparation method of the above MSCohi-O lenses, including the following steps:

culturing and expanding UCMSCs with a complete medium;

adding the complete medium into a culture dish, putting a bowl-shaped silicone hydrogel carrier in the culture dish upside down, and incubating the bowl-shaped silicone hydrogel carrier in an incubator at 30-40° ° C. for 0.5-2 h;

taking another new culture dish, adding the complete medium into the new culture dish, taking out the silicone hydrogel carrier incubated in the step 2), and placing the silicone hydrogel carrier vertically into the complete medium, with a bowl mouth facing up;

dissociating the UCMSCs cultured in the step 1), performing resuspension uniformly, dripping an absorbed cell suspension into a concave surface of the bowl-shaped silicone hydrogel carrier, and placing the cells into the incubator for culture after the cells are settled;

performing periodic washing and exchange of the complete medium, performing washing after the UCMSCs overspread the silicone hydrogel carrier, transferring the silicone hydrogel carrier to a lenses access box filled with the complete medium, and sealing the silicone hydrogel carrier with a sealing film; and irradiating the sealed silicone hydrogel carrier to obtain lenses.

The high oxygen permeability of the synthetic bowl-shaped silicone hydrogel carrier of the present disclosure helps to improve the cell viability of the UCMSCs and also helps to alleviate ocular discomfort of a user. Moreover, the bowl-shaped silicone hydrogel carrier has good compatibility with the UCMSCs and does not affect the growth of the UCMSCs.

In addition, the synthetic material of the bowl-shaped silicone hydrogel carrier is inexpensive and readily available to be low in production cost; the synthesis process is simple to operate, short in reaction time, guarantees the quality of the product while having a high production speed, and greatly improves the production efficiency. The prepared silicone hydrogel carrier has few impurities, and reduces adverse effects on the eyes.

In addition to oGVHD, the lenses of the present disclosure have also been found to be useful in the treatment of the Mooren's corneal ulcer. The etiology of the Mooren's corneal ulcer is unclear, but there is increasing evidence that the disease is an autoimmune disease. The bulbar conjunctival tissue adjacent to the Mooren's corneal ulcer is infiltrated by a large quantity of plasma cells, lymphocytes, histiocytes, macrophages, etc., with increased collagenase activity in the conjunctival tissue. The Mooren's corneal ulcer is idiopathic and is not associated with any systemic disease that may cause peripheral corneal ulcer.

In addition to oGVHD, the lenses of the present disclosure have also been found to be useful for inhibiting post-keratoplasty rejection. Keratoplasty is the final means to treat refractory keratopathies and corneal blindness for sight rehabilitating, but due to inflammation, vascularization and other factors, the survival rate of a graft after keratoplasty, especially penetrating keratoplasty, is still less than 50%. Immune rejection is the most prominent cause of the decrease in the survival rate of the graft, and keratoplasty failure.

DETAILED DESCRIPTION OF ILLUSTRATED EMBODIMENTS

The technical solutions in examples of the present disclosure are clearly and completely described in combination with accompanying drawings in the examples of the present disclosure, and obviously, the described examples are only a part of the examples of the present disclosure, but not all the examples of the present disclosure. Based on the examples of the present disclosure, other examples obtained by those of ordinary skill in the art without creative work all belong to the scope of protection of the present disclosure.

Example 1: an immunomodulatory effect of UCMSCs

Test on Inhibiting Proliferation of T Cells by UCMSCs

Figure 1:
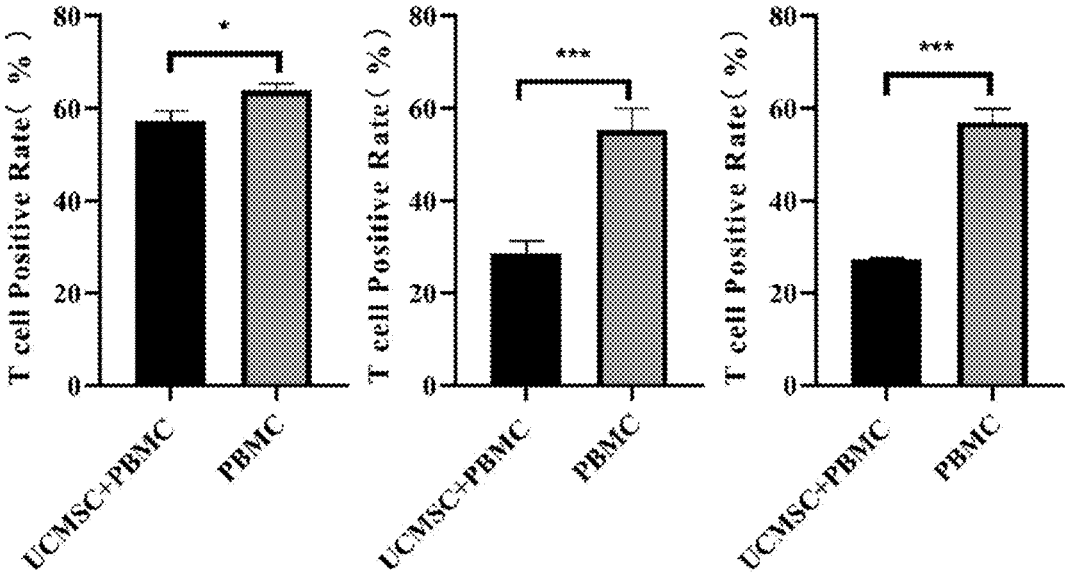
FIG. 1 is a statistical chart showing a proliferation inhibition of UCMSCs from a primary cell bank, a master cell bank and a working cell bank to T cells in Example 1 of the present disclosure.

UCMSCs ($2 \times 10^5$) were co-cultured with peripheral blood mononuclear cells (PBMCs, $1 \times 10^6$), and a control group was PBMC ($1 \times 10^6$) cultured alone, wherein culture systems were both 2 mL. Both a positive control group and a test group were added with phytohemagglutinin that is an agent for inducing proliferation of T cells, and after 4 days, the quantity of T cells was measured to be compared with the proliferation quantities of T cells under different conditions. The data showed that the proportion of T cells in the UCMSC+PBMC co-culture group was lower than that of T cells in the control group (see FIG. 1), and the proliferation inhibition rates of the UCMSCs from a primary cell bank, a master cell bank, and a working cell bank to T cells were calculated to be 10%, 48% and 52%, respectively (inhibition rate=(control group−test group)/(control group)×100%). This result indicates that UCMSCs from the three cell banks are able to inhibit the proliferation of T cells.

2. Inhibition of UCMSCs to Secretion of Inflammatory Factors by T Cells

Figure 2:
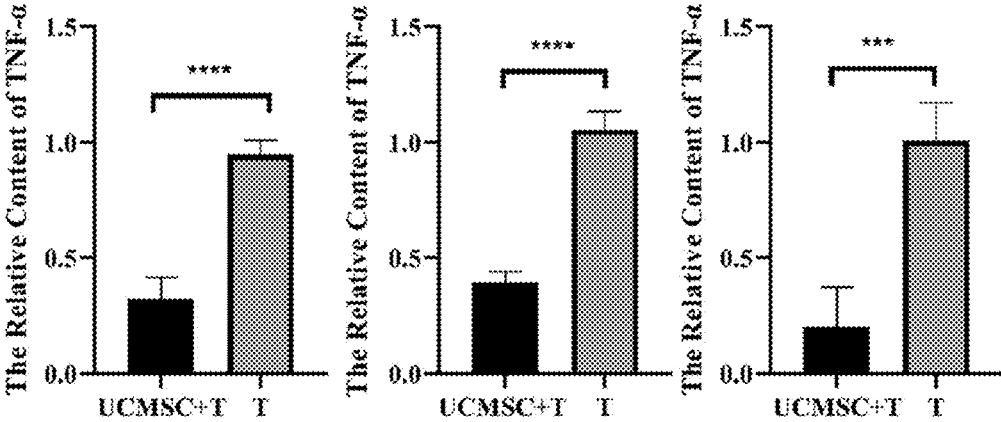
FIG. 2 is a statistical chart showing an inhibition of UCMSCs from a primary cell bank, a master cell bank and a working cell bank to secretion of TNF-α by T cells in Example 1 of the present disclosure.
Figure 3:
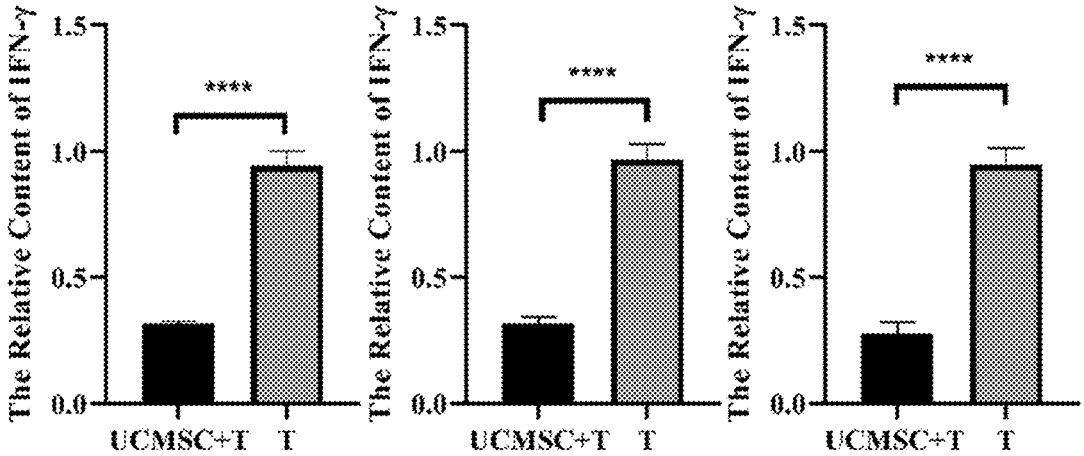
FIG. 3 is a statistical chart showing an inhibition of UCMSCs from a primary cell bank and a master cell bank to secretion of IFN-γ by T cells in Example 1 of the present disclosure.

After co-culture of UCMSCs ($2 \times 10^5$) with T cells ($1 \times 10^6$), inducers, i.e., 10 μL of 10 g/mL phorbol ester, 5 μL of 4 mg/mL brefeldin A, and 2 μL of 1 mg/mL ionomycin were added to induce T cells to secrete inflammatory factors, and the control group contained no UCMSCs. After 5 h of continued culture, T cells were collected in a culture medium and the secretion content of factors IFN-γ and TNF-α was detected by a qPCR method. The data showed that the contents of TNF-α (see FIG. 2) and IFN-γ (see FIG. 3) in the UCMSC+T cell group were lower than the contents in the control group, and the inhibition rates of the UCMSCs from the primary cell bank, the master cell bank and the working cell bank to secretion of TNF-α by T cells were calculated to be 66%, 63% and 80%, respectively, and the inhibition rates of the UCMSCs from the primary cell bank, the master cell bank and the working cell bank to secretion of IFN-γ by T cells were calculated to be 67%, 68% and 71%, respectively (inhibition rate=(control group−test group)/(control group)×100%). This result indicates that the UCMSCs from the three cell banks are able to inhibit secretion of IFN-γ and TNF-α by T cells.

3. Expression of IDO by UCMSCs Under Stimulation of Inflammatory Factors

Figure 4:
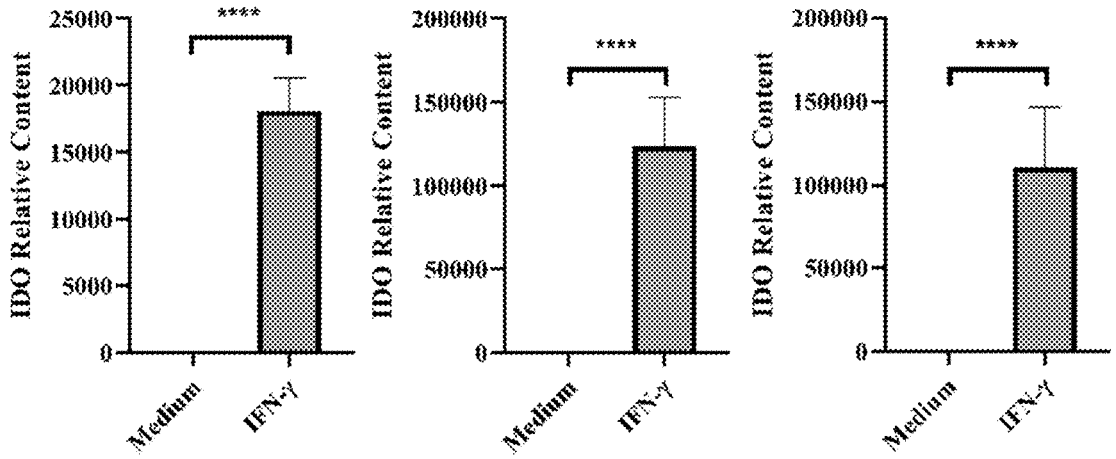
FIG. 4 is a statistical chart showing an amount of IDO expressed by UCMSCs from a primary cell bank, a master cell bank and a working cell bank induced by IFN-γ in Example 1 of the present disclosure.

UCMSCs were seeded in 6-well plates, 4 μL of 20 ng/mL inflammatory factor IFN-γ was added to the test group, and no IFN-γ was added to the control group. After 24 h of culture, UCMSCs were collected. The expression content of IDO was detected by the qPCR method. The data showed that the content of IDO expressed by UCMSCs after stimulation of the inflammatory factor IFN-γ is higher than the content in the control group (see FIG. 4), the content of IDO expressed by the UCMSCs from the primary cell bank, the master cell bank and the working cell bank induced by IFN-γ were calculated to be $2.1 \times 10^4$, $9.5 \times 10^4$, $7.3 \times 10^4$ times higher than the content of IDO in the corresponding control group, respectively (IDO expression multiplier=test group/control group). This result indicates that the inflammatory factors can induce the UCMSCs from the three cell banks to express IDO.

4. Promotion of Proliferation of Treg Cells by UCMSCs

Figure 5:
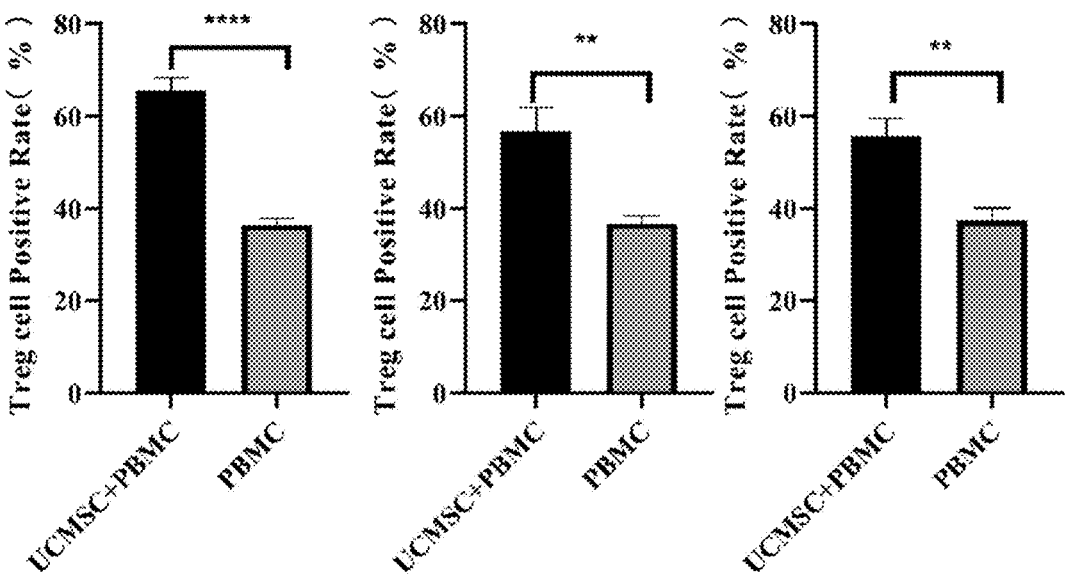
FIG. 5 is a statistical chart showing a promotion of UCMSCs from a primary cell bank, a master cell bank and a working cell bank to Treg cells in Example 1 of the present disclosure.

UCMSCs were seeded in 6-well plates and incubated with mitomycin C (final concentration being 10 mg/L) in an incubator for 20 min. PBMCs ($1 \times 10^6$/well), phytohemagglutinin (final concentration being 10 mg/L) and IL-2 (final concentration being 200 IU/mL) were added. Culture was performed for 16-20 h, centrifugation was performed to remove supernatant, and a fresh medium was added for culturing for 2 d. a PBMC suspension was collected, and flow cytometry detection was performed on a change in the ratio of Treg in PBMC (see FIG. 5). The proliferation increase rates of the UCMSCs from the primary cell bank, the master cell bank and the working cell bank boost to Treg cells were 44%, 35% and 33%, respectively (increase rate= (test group−control group)/control group×100%). This result indicates that UCMSCs from the three cell banks are able to promote the proliferation of Treg cells.

5. Inhibition of UCMSCs to Proliferation of Th1 Cells and Th17 Cells

Figure 6:
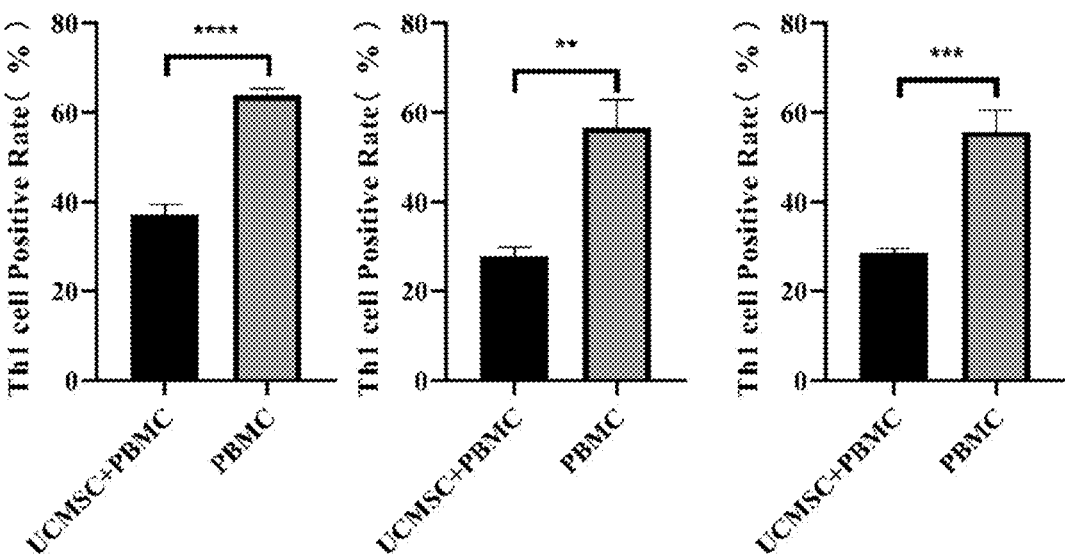
FIG. 6 is a statistical chart showing a proliferation inhibition of UCMSCs from a primary cell bank, a master cell bank and a working cell bank to Th1 cells in Example 1 of the present disclosure.
Figure 7:
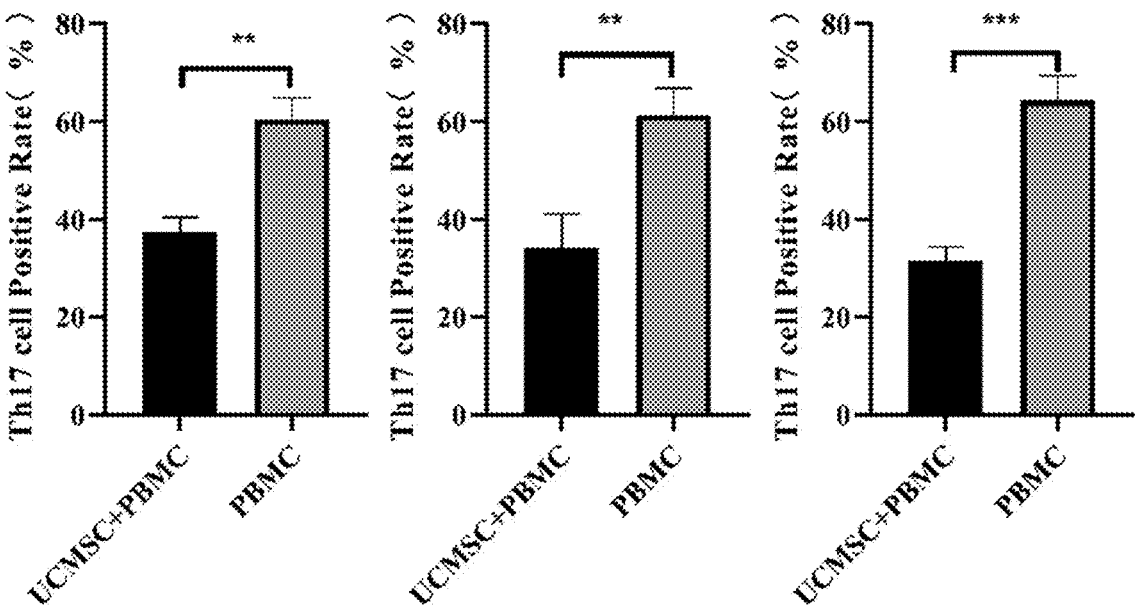
FIG. 7 is a statistical chart showing a proliferation inhibition of UCMSCs from a primary cell bank, a master cell bank and a working cell bank to Th17 cells in Example 1 of the present disclosure.

UCMSCs were seeded in 24-well plates ($1\times10^5$/well), mitomycin C (final concentration being 10 mg/L) was added next day, incubation was performed in an incubator for 20 min, supernatant was removed, DPBS (250 μL/well) was used to wash 2 times, and PBMCs ($1\times10^6$/well) were added. Culturing was performed for 48 h, 2 L of Leukocyte Activation Cocktail with BD GolgiPlug was added and culturing was continued for 5 h. PBMCs were collected and flow cytometry detection was performed. The data showed that the proportions of Th1 cells (see FIG. 6) and Th17 cells (see FIG. 7) in the UCMSC+PBMC co-culture group were lower than that of Th1 cells and Th17 cells in the control group, respectively. The proliferation inhibition rates of the UCMSCs from the primary cell bank, the master cell bank and the working cell bank to Th1 cells were 42%, 51% and 48% respectively; and the proliferation inhibition rates of the UCMSCs from the primary cell bank, the master cell bank and the working cell bank to Th17 cells were 38%, 44% and 51% respectively (inhibition rate=(control group−test group)/(control group)×100%). This result indicates that UCMSCs from the three cell banks are able to inhibit the proliferation of Th1 and Th17 cells Example 2: Preparation of bowl-shaped silicone hydrogel carrier Preparation of an organosilicone monomer: 500 g of hydrogenated silicone oil (molecular weight 4000), 34.65 g of allyl methacrylate, and 0.03 g of a polymerization inhibitor hydroquinone are weighed and are stirred in 600 g of a solvent xylene uniformly to obtain a mixture, the mixture is heated to 35° C. under a nitrogen atmosphere, 0.06 g of chloroplatinic acid is added, and reaction is performed for 18 h at 40° ° C. Distillation under reduced pressure is then performed to remove the solvent as well as components with a low boiling point to obtain the organosilicone monomer.

Preparation of the bowl-shaped silicone hydrogel carrier: 25 parts of organosilicone monomer, 58 parts of hydrophilic monomer (in which 30 parts of hydroxyethyl methacrylate, 16 parts of N-vinylpyrrolidone, and 12 parts of N-methyl-N-vinylacetamide), 0.7 part of a cross-linking agent ethylene glycol dimethacrylate, 0.5 part of an initiator azobisisobutyronitrile, and 30 parts of a solvent isopropanol are mixed uniformly in parts by weight to obtain polymeric liquid, a plastic mold is filled with the polymeric liquid, nitrogen is introduced, heat curing is performed, and an obtained polymer rod after curing is lathed to be of a button shape, and finally the button-shaped material is cut on two sides to produce the bowl-shaped silicone hydrogel carrier.

Example: 3: Preparation of MSCohi-O Lenses

Culture and Expansion of UCMSCs 6 mL of the complete medium is plated in a T75 culture flask in advance and is incubated in an incubator at 37° C. for 1 h. UCMSCs are taken from a liquid nitrogen tank, rapidly dissolved in a water bath at 37° C., transferred to a 15 mL centrifuge tube filled with 10 mL DF (10) (DMEM/F12: 9 mL, HPL: 1 mL), and centrifuged at 1000 rpm for 5 min, and after centrifugation, the cells are resuspended with 15 mL of the complete medium, and transferred to a glued T75 culture flask, and the complete medium is changed every other day.

UCMSCs are sub-cultured and cryopreserved when growing to be about 80% confluence, a T75 culture flask is glued in advance, the medium is discarded, washing is performed twice with DPBS (Dulbecco's phosphate buffered saline), 0.25% tryptic solution is added for digestion for 2.5 min, the digestion is stopped with 6 mL DF(10), the cells on the wall are blown down, the culture flask is washed with 6 mL DF(-) (DF(10) without HPL), and the cells are transferred to a 50 mL centrifuge tube and counted. 1 million cells are transferred into a 15 mL centrifuge tube, centrifuged at 1,000 rpm for 5 min, resuspended with 15 mL of the complete medium with the ternary antibody after centrifugation, and transferred to a glued T75 culture flask, and the complete medium is changed every other day. Cells in the 50 mL centrifuge tube are resuspended with 2 mL cryopreservation solution to form a single cell suspension, and cryopreservation is performed at 2 million per tube.

Preparing Cell Suspension

Cell growth is observed with a microscope and photographed: cells have a normal morphology and are adherent by about 80% confluence.

During sub-culturing of the cells, the dissociated cell suspension is counted and centrifuged. After centrifugation to remove the supernatant, resuspension is performed with a certain amount of complete medium to make a cell density of 5 million/mL for standby.

Seeding of UCMSCs into the Carrier

A complete medium is equilibrated at room temperature. 1 mL of the complete medium is added into a 35 mm culture dish, a bowl-shaped silicone hydrogel material is put into the culture dish upside down by using tweezers and support rods special for silicone hydrogel material, and the inside of the bowl-shaped silicone hydrogel is infiltrated with the complete medium, and is incubated in an incubator for 37° ° C. for 1 h.

Another new 35 mm culture dish is taken and 2 mL of the complete medium is added. The bowl-shaped silicone hydrogel material is carefully removed from the incubator with a bowl mouth facing up and is placed vertically into the medium.

The cultured proliferated UCMSC cell suspension is resuspended uniformly, and 100 μL (approximately 0.5 million cells) of the cell suspension is dripped into a concave surface of the silicone hydrogel material, after the cells are photographed with a microscope after being settled and are carefully placed in an incubator for culture. After 1-2 h, 500 L of the complete medium is added into the culture dish so that the outer medium level of the bowl-shaped silicone hydrogel material is level with the edge. The complete medium is changed next day.

Change of the Complete Medium

The complete medium is equilibrated at room temperature.

Cell growth is observed with a microscope and photographed: cells have been adherent to form multiple layers of adherent cells.

The medium is discarded from the culture dish and washed by adding 2 mL DPBS, which is repeated once. 3 mL of the complete medium is added into a 12-well plate, and the washed carrier loaded with UCMSCs is immersed into the medium completely for continued culture. The complete medium is changed every other day.

Access of Lenses

The complete medium is equilibrated at room temperature.

Cell growth in the material is observed with a microscope and photographed: the cell status is good, the overall density is large, there is no voids and no cell mass.

The medium is discarded, added with 2 mL DPBS, and washed with gentle shaking to be discarded. The process is repeated once. 2.5 mL of the complete medium is added into a lenses access box, the washed lenses are completely immersed in the medium, sealed with a sealing film, and placed in an irradiator in which the irradiation dose is set to be 15 Gy to obtain MSCohi-O lenses after irradiation.

Figure 8:
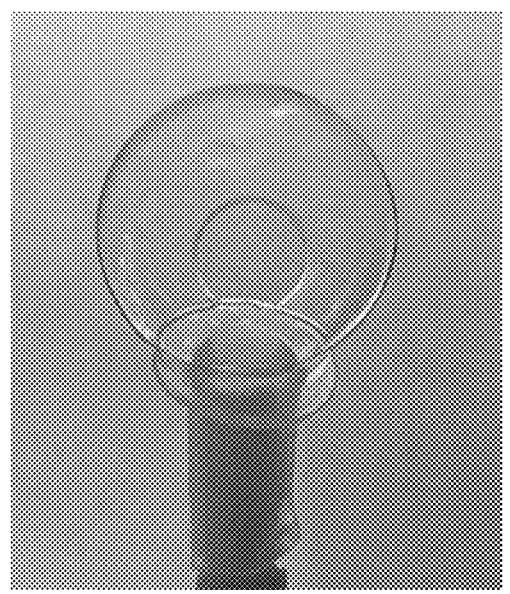
FIG. 8 shows MSCohi-O lenses in Example 3 of the present disclosure.

In practical application, a small spacer is placed in the middle of the silicone hydrogel material before UCMSCs are seeded, and after the UCMSCs are adherent, the spacer is uncovered to form a circular blank area in the middle of the bowl-shaped silicone hydrogel material, wherein the circular blank area has a diameter of 2-6 mm, which is specifically as shown in FIG. 8. When the lenses are placed in the human eyes, the cells can form a thin film on the lenses, which can cause the visual field of the human eyes to be somewhat blurred. The circular blank area is formed in the middle of the silicone hydrogel carrier where the visual field is not affected by the lenses. An UCMSC lens without a circular blank area is put into one of the eyes, an UCMSC lens with a circular blank area is placed in the other one of the eyes, or UCMSC lenses with circular blank areas are put into the two eyes, which can ensure not only both therapeutic or palliative effects of the UCMSC lenses on the eyes, and also a clear visual field of the human eyes, without affecting normal life.

Example 4: Characteristic Properties of MSCohi-O lenses

Cell Activity of UCMSCs Loaded on MSCohi-O Lenses

After MSCohi-O lenses were prepared, the quantity of cells was $1.5 \times 10^5$ after 48 h, with the cell viability of 97%; and the quantity of cells after 72 h was $1.4 \times 10^5$, with the cell viability of 95%. After MSCohi-O lenses were prepared, 48 h and 72 h later, the cell viabilities of cells on the lenses was 90% or above, and the quantity of cells was in the range of $1.0 \sim 2.0 \times 10^5$, which was up to the standard.

Storage Stability of MSCohi-O Lenses

MSCohi-O lenses were stored at room temperature for 0 h, 2 h, 4 h, 6 h, 8 h, 24 h and 48 h. The UCMSCs on the MSCohi-O lenses were then examined. The results indicated that the cell morphology was irregularly triangular or fusiform, with a vortex-like (S-shaped) distribution. The cell viabilities were between 93-99% and the quantity of cells was $1.1 \sim 1.6 \times 10^5$. After storage of MSCohi-O lenses at room temperature for up to 48 h, there was no difference in morphology on the cells loaded on MSCohi-O lenses, the cell viabilities were 90% or above, and the quantity of cells was in the range of $1.0 \sim 2.0 \times 10^5$, which met the acceptance criteria. These results show that MSCohi-O lenses can be stored at room temperature for 48 h.

3. Biological Effectiveness of UCMSCs Subjected to Irradiation

Figure 9:
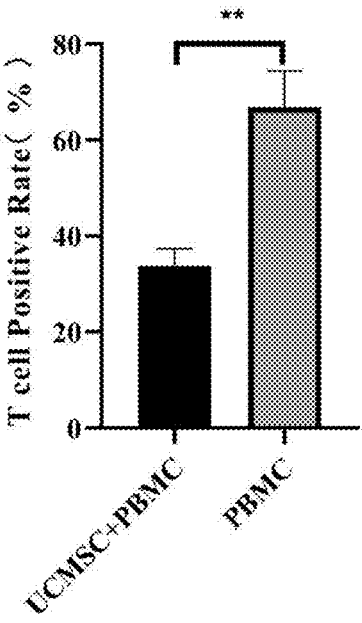
FIG. 9 is a statistical chart showing a proliferation inhibition of UCMSCs subjected to irradiation to T cells in Example 4 of the present disclosure.
Figure 10:
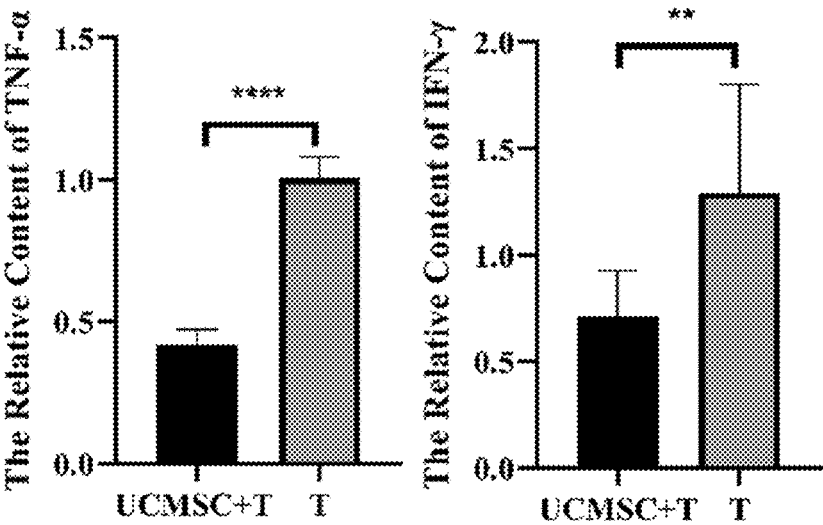
FIG. 10 is a statistical chart showing an inhibition of UCMSCs subjected to irradiation to secretion of TNF-α and IFN-γ by T cells in Example 4 of the present disclosure.
Figure 11:
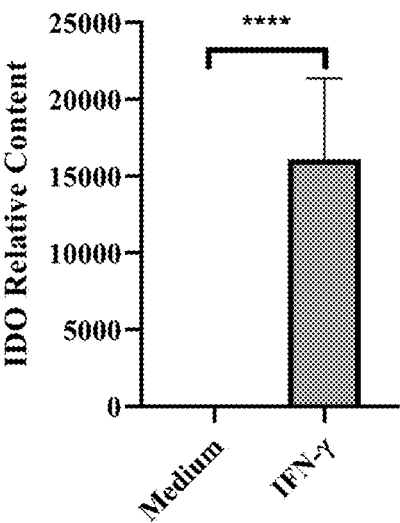
FIG. 11 is a statistical chart showing an amount of IDO expressed by UCMSCs subjected to irradiation induced by IFN-γ in Example 4 of the present disclosure.
Figure 12:
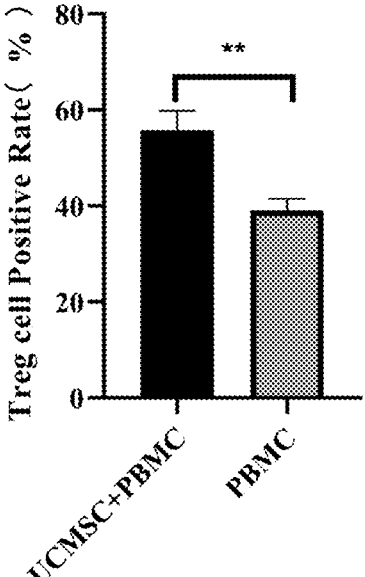
FIG. 12 is a statistical chart showing a promotion of UCMSCs subjected to irradiation to Treg cells in Example 4 of the present disclosure.
Figure 13:
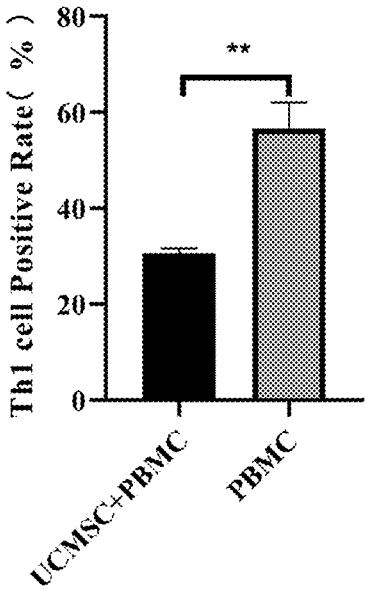
FIG. 13 is a statistical chart showing a proliferation inhibition of UCMSCs subjected to irradiation to Th1 cells in Example 4 of the present disclosure.
Figure 14:
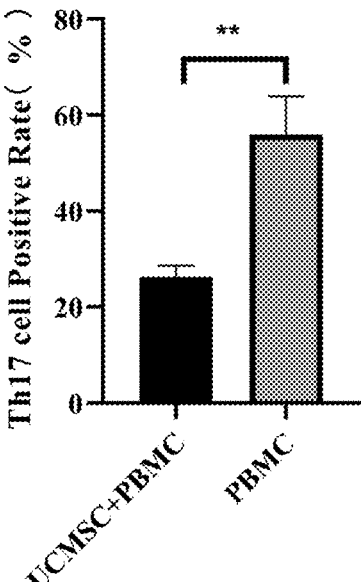
FIG. 14 is a statistical chart showing a proliferation inhibition of UCMSCs subjected to irradiation to Th17 cells in Example 4 of the present disclosure.

According to the preceding test methods, the proliferation inhibition rate of UCMSCs subjected to irradiation to T cells was 50% (data shown in FIG. 9); the inhibition rate of UCMSCs subjected to irradiation to secretion of TNF-α by T cells was 59% and the inhibition rate of UCMSCs subjected to irradiation to secretion of IFN-γ by T cells was 45% (data shown in FIG. 10); the content of IDO expressed by UCMSCs subjected to irradiation induced by IFN-γ was $5.3 \times 10^3$ times higher than that of the control group (data shown in FIG. 11). The proliferation increase rate of UCMSCs subjected to irradiation to Treg cells was 30% (data shown in FIG. 12), and the proliferation inhibition rates of UCMSCs subjected to irradiation to Th1 cells and Th17 cells were 46% (data shown in FIG. 13) and 53% (data shown in FIG. 14), respectively. These results indicate that UCMSCs subjected to irradiation have the ability to inhibit proliferation of T cells, inhibit secretion of IFN-γ and TNF-α inflammatory factors by T cells, express IDO with IFN-γ stimulation, promote proliferation of Treg cells, and inhibit proliferation of Th1 cells and Th17 cells, thereby exerting the immunomodulatory effects.

Example 5: Animal Tests for Detection on Effects of MSCohi-O Lenses for Treating oGVHD There is no animal model of oGVHD at present. Through literature search and consultation with ocular specialists, we selected the "New Zealand Rabbit Corneal Alkali-Burn Model" from existing ophthalmic animal models to evaluate the efficacy of the product in this article: 1) in the field of toxicological and pharmacokinetic evaluation, rabbits are the preferred animal species for non-clinical evaluation of ophthalmic drugs, and many recent ophthalmic studies use New Zealand rabbits as model animals; 2) there is no pigment effect in ocular evaluation based on the albinism characteristics of rabbits; 3) compared to rodents, rabbits have more anatomical and biochemical features in common with humans, including longer lifespan and larger eyes; 4) corneal alkali-burn can cause inflammation of the ocular surface and corneal ulcer, which are the same as the main clinical manifestations of oGVHD due to the penetration and strong destruction of alkaline substances to the tissues; 5) UCMSCs can effectively alleviate autoimmune diseases in rabbits, have low immunogenicity and do not elicit immune rejection even if used allogenically or across species. The test was conducted as follows. After anesthesia of New Zealand rabbits, a piece of filter paper first soaked with NaOH was only applied at the cornea of the left eyes of each rabbit for 30 seconds. A sodium chloride injection for injection was used to wash the lesion, and then lens wearing was performed; a total of 4 groups were set up: a blank control group, an alkali-burn group, an alkali-burn+blank lenses group, an alkali-burn+MSCohi-O lenses group, wherein there were 5 rabbits in each group, with females and males. The left eyes were sutured, and were applied with tobramycin eye cream, and the rabbits returned to rearing cages. The rabbits required surgical anesthesia and suturing when MSCohi-O lenses were worn, and new lenses were changed once on the 0th, 3rd, 7th, 10th and 14th day respectively, with a total of 5 times of lenses wearing. On the 3rd, 7th, 10th, 14th and 17th day after wearing MSCohi-O lenses, corneal neovascularization was tested and corneal injury area was examined by corneal fluorescence staining after lenses removal, the corneas of the New Zealand rabbits were taken on 17th day to detect inflammatory neovascularization and injury area of the samples, and qPCR was performed to detect the expressions of anti-inflammatory factors (IL-4), pro-inflammatory factors (IL-6, TNF-α, IL-23, MMP1, MMP2 and MMP9), and growth factors (VEGF).

Figure 15:
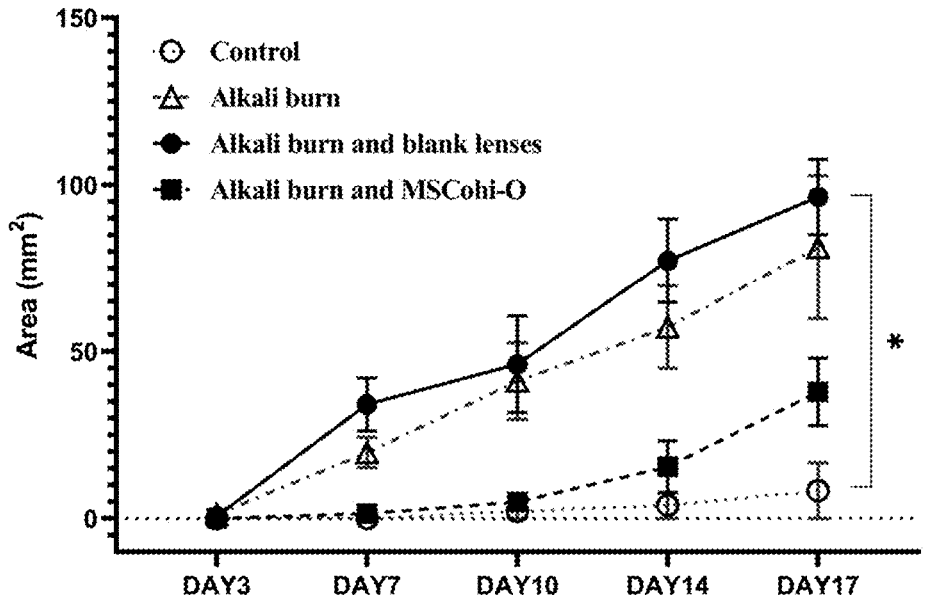
FIG. 15 is a statistical chart showing neovascular area in Example 5 of the present disclosure.

The data showed:

Calculation for the neovascular area: the neovessels grew most rapidly in both the alkali-burn group and the alkali-burn+blank lenses group, with calculated areas of $81 \text{ mm}^2$ and $96 \text{ mm}^2$, respectively; neovessels in the alkali-burn+ MSCohi-O lenses group grew slowly and basically no longer grew at the later stage of observation, with a calculated area of $40 \text{ mm}^2$; neovessels in the blank control group grew similarly, and basically did not grow during the observation period, with a calculated area of no more than $15 \text{ mm}^2$ (see FIG. 15).

Figure 16:
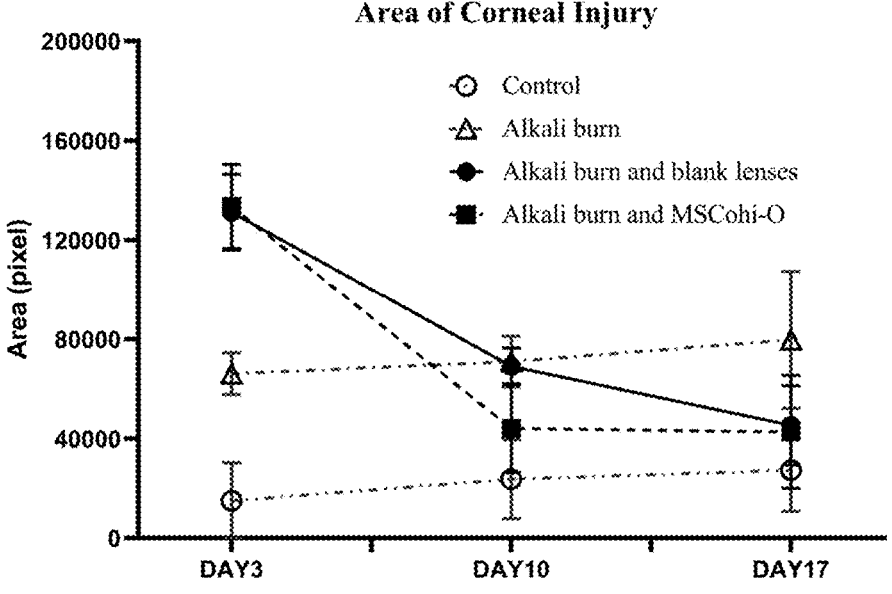
FIG. 16 is a statistical chart showing a fluorescein staining area in Example 5 of the present disclosure.

Calculation for the fluorescein staining area: in the alkali-burn+blank lenses group and the alkali-burn+MSCohi-O lenses group, the calculated fluorescein staining areas of corneas decreased slowly during the observation period, which were respectively 45000 (pixel) and 43000 (pixel); in the alkali-burn group, the calculated fluorescein staining area of corneas remained unchanged during the observation period, stabilizing at 79000 (pixel); and in the blank control group, calculated fluorescein staining areas of corneas were 27000 (pixel) (see FIG. 16).

Figure 17:
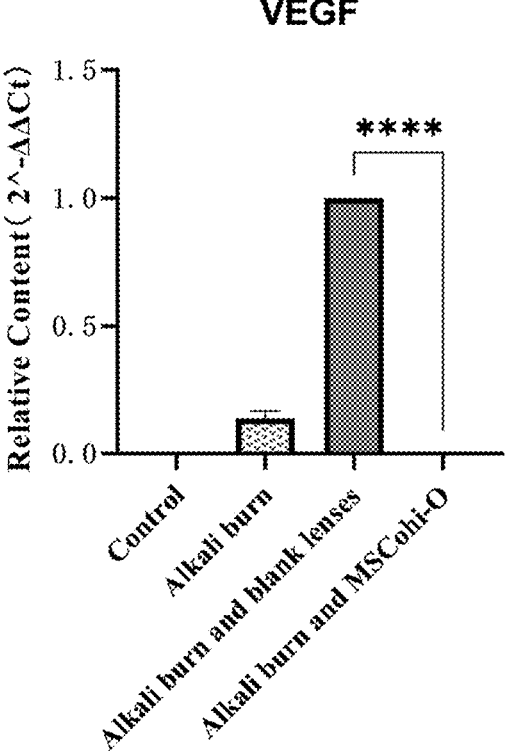
FIG. 17 is a graph showing a content of a growth factor (VEGF) in Example 5 of the present disclosure.

Content detection of Growth factor (VEGF): in the alkali-burn+blank lenses group, the alkali-burn+blank lenses group had the largest secretion content, followed by the alkali-burn group, the alkali-burn+MSCohi-O lenses group, and the blank control group (see FIG. 17).

Figure 18:
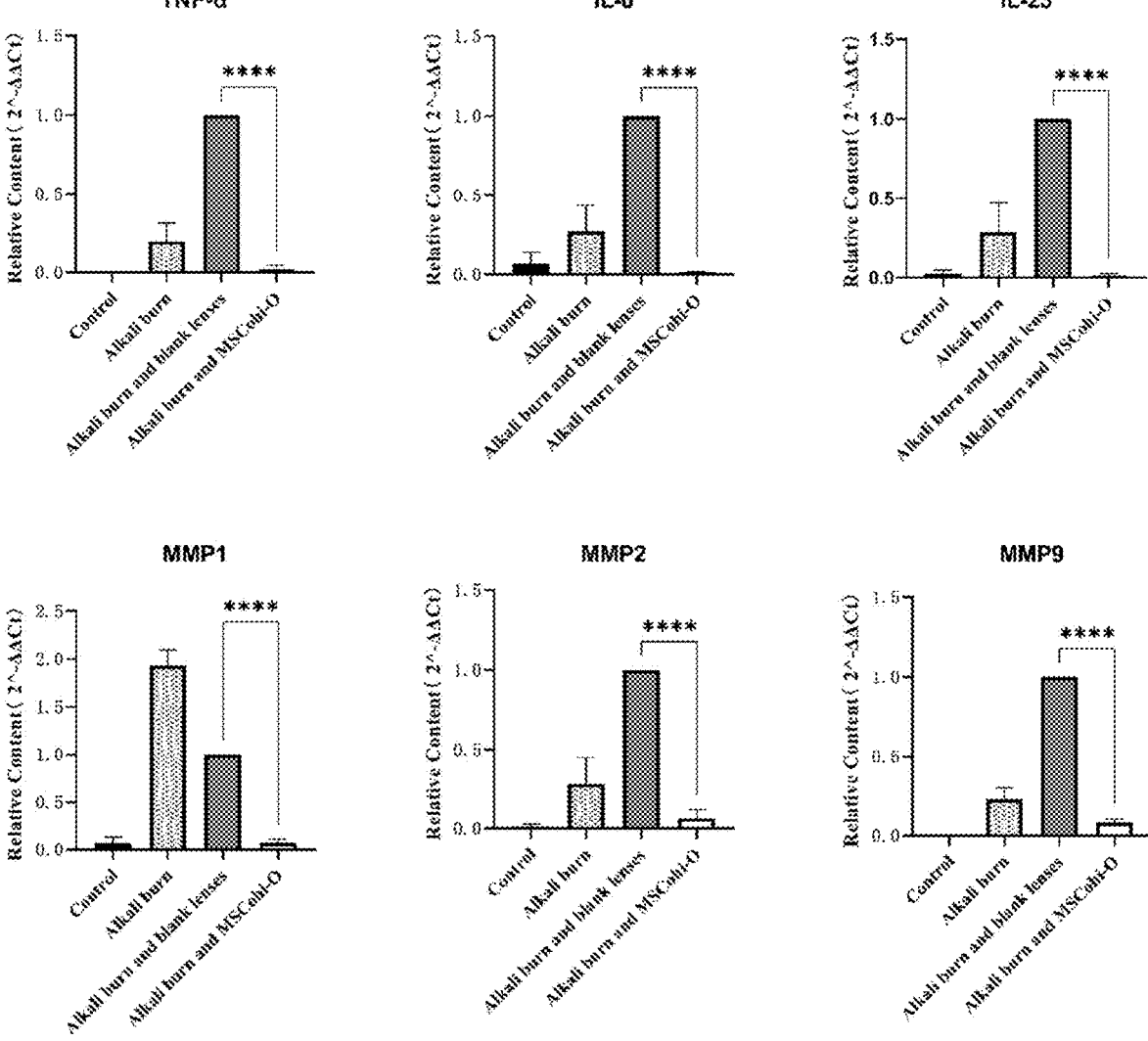
FIG. 18 is a graph showing detection of the content of a pro-inflammatory factor in Example 5 of the present disclosure.

Content detection of pro-inflammatory factors: Pro-inflammatory factor content detection: (TNF-α, IL-6, IL-23, MMP1, MMP2, MMP9) alkali-burn+blank lenses group had the largest secretion content, followed by the alkali-burn group and the alkali-burn+MSCohi-O lenses group, and the blank control group had the lowest secretion content (see FIG. 18).

Figure 19:
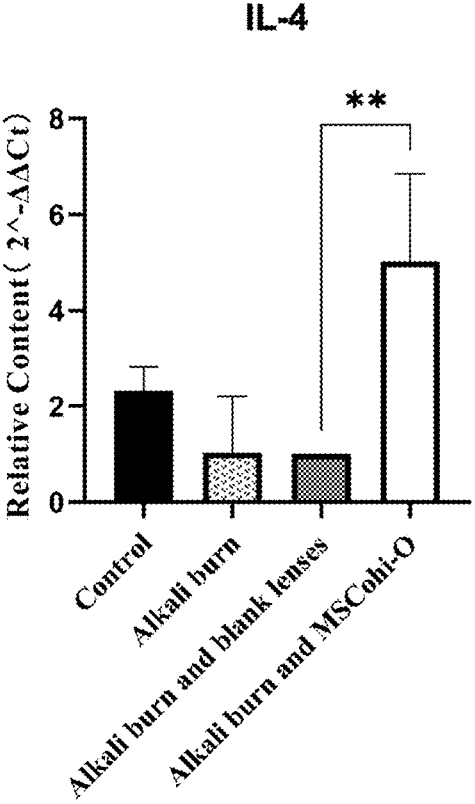
FIG. 19 is a graph showing detection of the content of an anti-inflammatory factor (IL-4) in Example 5 of the present disclosure.

Content detection of anti-inflammatory factors (IL-4): the alkali-burn+MSCohi-O lenses group had the largest secretion content, followed by the blank control group, the alkali-burn group, and the alkali-burn-blank lenses group (see FIG. 19).

These results indicate that: 1) MSCohi-O lenses can inhibit the growth of fundus neovascularization; 2) MSCohi-O lenses can reduce the extent of corneal damage in animals; 3) MSCohi-O lenses can inhibit the expression of the growth factor VEGF; 4) MSCohi-O lenses groups can inhibit the expression of the pro-inflammatory factors TNF-α, IL-6, IL-23, MMP1, MMP2 and MMP9; and 5) MSCohi-O lenses can promote the expression of the anti-inflammatory factor IL-4.

Therefore, MSCohi-O lenses can promote the healing of corneal ulcer by reducing inflammation on the ocular surface due to alkali-burns in New Zealand rabbits and inhibiting the release of associated inflammatory factors. The results of the test on New Zealand rabbit corneal alkali-burn model indicate that MSCohi-O lenses have the feasibility of inhibiting immune response observed in severe oGVHD.

Example 6: Clinical Study Initiated by Investigators to Detect the Effect of MSCohi-O Lenses for Treating oGVHD Volunteer 1: Male, 42 Years Old allo-HSCT was performed on Nov. 28, 2017. Ocular rejection symptoms appeared after September 2018, followed by a diagnosis of oGVHD. In September 2020, the patient perceived dry eyes and pain (unaided vision: 1.0 (right eye), 1.1 (left eye); intraocular pressure: 13 mmHg (right eye); 16 mmHg (left eye)). Symptoms were temporarily relieved after applying artificial tears and autologous serum eye drops, but became worse after 2 months with maintenance treatment of eye drops. The slit lamp results showed that the cornea of both eyes had ulcers, with an ulcer area of 25.58 mm$^2$ in the cornea of the left eye and 21.83 mm$^2$ in the right eye.

The patient began wearing MSCohi-O lenses on November 2020 (unaided vision: 1.0 (right eye), 1.1 (left eye); intraocular pressure: 13 mmHg (right eye); 14 mmHg (left eye)) with 5 times of changes of the lenses in total. In December 2020, the patient reported a loss of pain and reduced dryness (unaided vision: 1.0 (right eye), 1.1 (left eye); intraocular pressure: 13 mmHg (right eye); 15 mmHg (left eye)). Slit-lamp photography showed that the corneal epithelium was rapidly repaired, the corneal transparency was gradually recovered, the fluorescein staining area was reduced than before, the corneal fluorescein staining area of the cornea of the left eye (OS) was 16.19 mm$^2$, with 37% smaller than before, and the fluorescein staining area of the cornea of the right eye (OD) was 16.43 mm$^2$, with 25% smaller than before. During follow-up visits, the patient felt well without any adverse events.

Figure 20:
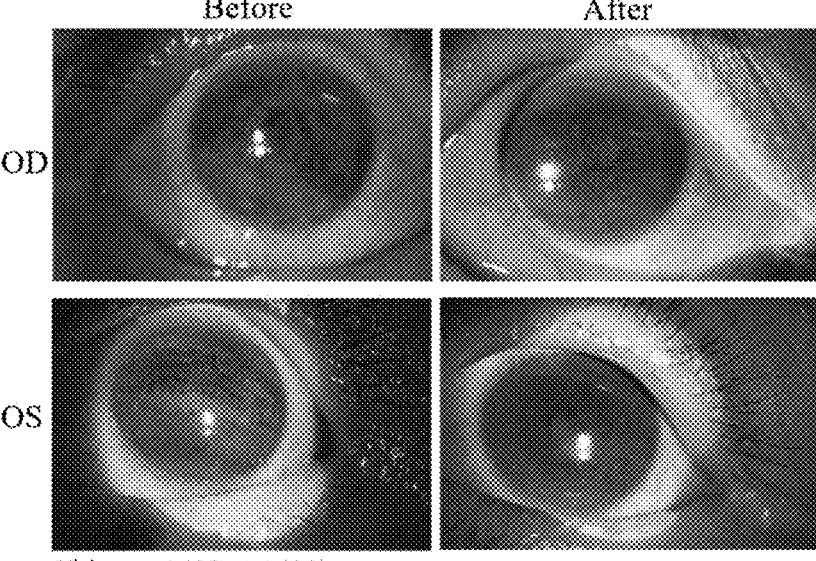
FIG. 20 is a graph showing an effect of MSCohi-O lenses for treating volunteer 1 in Example 6 of the present disclosure.

A comparison of the ocular status of the volunteer before and after wearing MSCohi-O lenses is shown in FIG. 20.

Volunteer 2: Female, 39 Years Old allo-HSCT was performed in September 2013. Ocular rejection occurred in 2014. The diagnosis of oGVHD was confirmed in 2015. In October 2020, the patient developed intense foreign object sensation (unaided vision: 1.1 (right eye), 0.9 (left eye); intraocular pressure: 18 mmHg (right eye), 14 mmHg (left eye)). Symptoms were temporarily relieved after 1 month treatment with artificial tears, meibomian gland massage, immunosuppressant cyclosporine, and tacrolimus. The patient received light pulse therapy, and has been subjected to maintenance treatment by eye drops. The slit lamp results showed significant opacification of the corneas in both eyes of the patient, ulceration of the cornea in the left eye with an area of 20.18 mm$^2$, and ulceration of the entire cornea in the right eye with an area of 24.64 mm$^2$.

Figure 21:
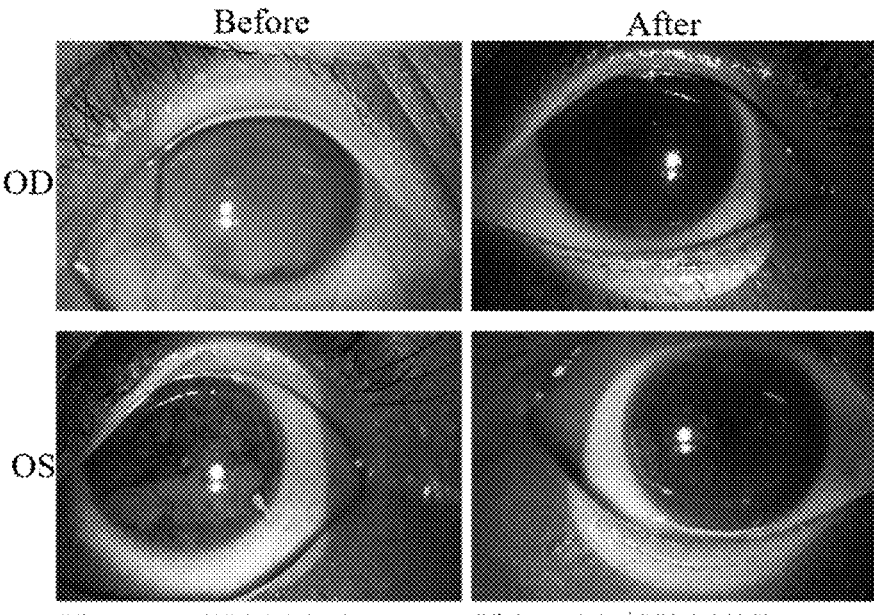
FIG. 21 is a graph showing an effect of MSCohi-O lenses for treating volunteer 2 in Example 6 of the present disclosure.

The patient began wearing MSCohi-O lenses in December 2020 (unaided vision: 1.1 (right eye), 0.9 (left eye); intraocular pressure: 15 mmHg (right eye); 14 mmHg (left eye)), with a total of 10 times of lenses wearing. In January 2021, the patient reported improved foreign object sensation (unaided vision: 1.1 (right eye), 0.9 (left eye); intraocular pressure: 18 mmHg (right eye); 13 mmHg (left eye)). Slit-lamp photography showed that diffuse punctate loss of corneal epithelium in both eyes was relieved than before, and the corneas in both eyes recovered to be transparent. The fluorescein staining area was reduced than before. The corneal fluorescein staining area of the cornea of the left eye (OS) was 6.81 mm$^2$, with 66% smaller than before, and the fluorescein staining area of the cornea of the right eye (OD) was 2.35 mm$^2$, with 90% smaller than before (FIG. 21). During follow-up in May 2021, the patient felt well and was in complete remission without any adverse events.

A comparison of the ocular status of the volunteer before and after wearing MSCohi-O lenses is shown in FIG. 21.

Example 7: Clinical Study Initiated by Investigators to Detect the Effect of MSCohi-O Lenses for Treating Mooren's Corneal Ulcer Volunteer 3: Female, 68 Years Old The patient was diagnosed with diabetes in 2012. On Aug. 10, 2022, the left eye was red with foreign object sensation for 3 months, filamentous secretions, and pain sensation by compression (unaided vision: 0.2 (right eye), 0.5 (left eye); intraocular pressure: 19 mmHg (right eye), 16 mmHg (left eye)). Eye drops with 0.1% fluorometholone and pronamol were applied. The slit lamp results showed conjunctival hyperemia and scleral hyperemia in the left eye of the patient.

The patient began wearing MSCohi-O lenses in October 2022 for a total of 6 times. In November 2022, the patient reported a great reduction in eye redness and a loss of foreign object sensation (unaided vision: 0.4 (right eye), 0.4 (left eye); intraocular pressure: 14 mmHg (right eye), 19 mmHg (left eye)). Slit-lamp photography showed great improvement in conjunctival injection and scleral injection, and the ulcer area in the left eye was decreased than before.

Figure 22:
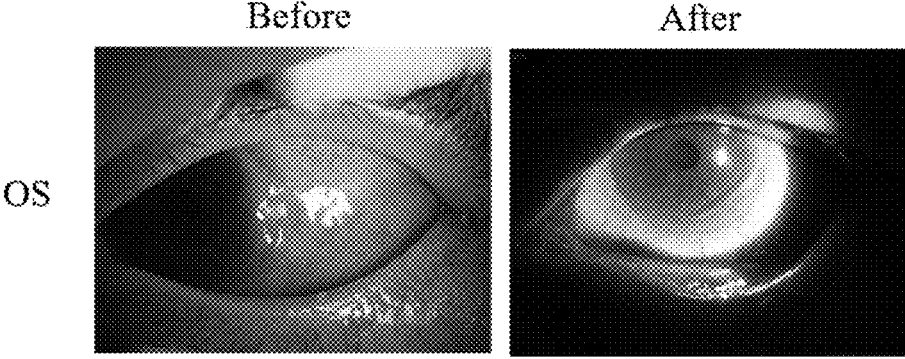
FIG. 22 is a graph showing an effect of MSCohi-O lenses for treating volunteer 3 in Example 7 of the present disclosure.

A comparison of the ocular status of the volunteer before and after wearing MSCohi-O lenses is shown in FIG. 22.

Example 8: Clinical Study Initiated by Investigators to Detect the Effect of MSCohi-O Lenses for Inhibiting Post-Keratoplasty Rejection Volunteer 4: Male, 60 Years Old Penetrating keratoplasty was performed in March 2021 due to corneal ulcer followed by postoperative rejection, and penetrating keratoplasty was performed again in February 2022 (unaided vision: 0.25 (right eye); intraocular pressure: 15 mmHg (right eye)). The patient developed postoperative red eyes and pain, and was treated by wearing corneal bandage lenses. The patient also had uveitis and systemic ankylosing spondylitis, which were treated with anti-adalimumab. His eyes were still red, and the central epithelial defect of the cornea had not healed for a long time. The slit lamp results showed that the corneal ulcer area of the right eye was 23.13 mm$^2$.

Figure 23:
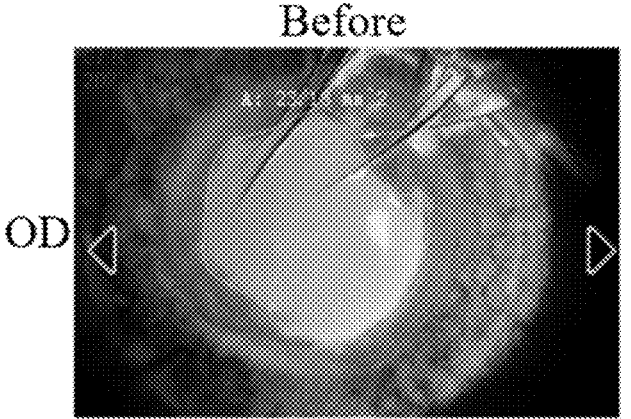
FIG. 23 is a graph showing an effect of MSCohi-O lenses for treating volunteer 4 in Example 8 of the present disclosure.
Figure 23:
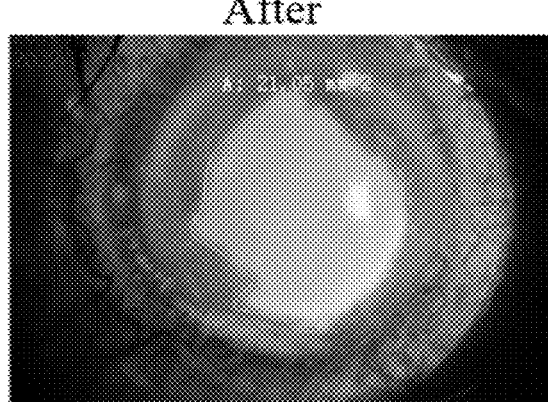

The patient began wearing MSCohi-O lenses in November 2022 (unaided vision: 0.25 (right eye); intraocular pressure: 16 mmHg (right eye)). In December 2022, the eye redness symptoms were significantly diminished (unaided vision: 0.4 (right eye); intraocular pressure: 14 mmHg (right eye)), epithelial defect area was reduced, and the corneal ulcer area of the right eye was 21.05 mm$^2$ (FIG. 23). During follow-up in December 2022, the patient felt well and was in gradual improvement without any adverse events.

A comparison of the ocular status of the volunteer before and after wearing MSCohi-O lenses is shown in FIG. 23.

The above examples are merely to illustrate the technical solutions of the present disclosure and are not to limit the scope of protection of the present disclosure. Although the present disclosure has been described in detail with reference to the preferred examples, it will be understood by those skilled in the art that the technical solutions of the present disclosure may be modified or equivalent replaced without departing from the spirit and scope of the technical solution of the present disclosure.

The invention claimed is:

1. Lenses for treating ocular diseases, comprising a bowl-shaped silicone hydrogel carrier and umbilical cord mesenchymal stem cells loaded on the carrier; wherein the bowl-shaped silicone hydrogel carrier is polymerized from an organosilicone monomer and a hydrophilic monomer under an action of a cross-linking agent and an initiator;
the organosilicone monomer is polymerized from a hydrogenated silicone oil and allyl methacrylate under the action of a polymerization inhibitor and a catalyst; and the umbilical cord mesenchymal stem cells are treated with irradiation.

2. The lenses for treating ocular diseases of claim 1, wherein the hydrophilic monomer is a mixture of hydroxyethyl methacrylate, N-vinylpyrrolidone and N-methyl-N-vinylacetamide.

3. The lenses for treating ocular disease of claim 2, wherein the cross-linking agent is ethylene glycol dimethacrylate, and wherein the initiator is azobisisobutyronitrile.

4. The lenses for treating ocular diseases of claim 3, wherein a weight ratio of the organosilicone monomer to the hydrophilic monomer to the cross-linking agent to the initiator is (25~30):(55~60):(0.6~0.8):(0.4~0.6).

5. The lenses for treating ocular diseases of claim 1, wherein the polymerization inhibitor is hydroquinone, and the catalyst is chloroplatinic acid.

6. The lens for treating ocular diseases of claim 5, wherein a weight ratio of the hydrogenated silicone oil to allyl methacrylate to the polymerization inhibitor to the catalyst is (500~520):(34~35):(0.02~0.04):(0.06~0.08).

7. The lenses for treating ocular diseases of claim 1, wherein the bowl-shaped silicone hydrogel carrier has a diameter of 12~15 mm, a radius of curvature of 8.3~8.6 mm, a center thickness of 0.07~0.09 mm, and an oxygen permeability of 135 DK/t or above.

8. The lenses for treating ocular diseases of claim 1, wherein a circular blank area without the umbilical cord mesenchymal stem cells is disposed in a middle of the bowl-shaped silicone hydrogel carrier, and the circular blank area has a diameter of 2~6 mm.

9. The lenses for treating ocular diseases of claim 1, wherein a quantity of the umbilical cord mesenchymal stem cells loaded on the carrier is 1.0~2.0×10$^5$.

10. A preparation method of lenses for treating ocular diseases, comprising steps as follows:
1) culturing and expanding umbilical cord mesenchymal stem cells with a complete medium;
2) adding a complete medium into a culture dish, putting a bowl-shaped silicone hydrogel carrier in the culture dish upside down, and incubating the bowl-shaped silicone hydrogel carrier in an incubator at 30-40° ° C. for 0.5-2 h;
3) taking another new culture dish, adding the complete medium into the new culture dish, taking out the silicone hydrogel carrier incubated in step 2), and placing the silicone hydrogel carrier vertically into the complete medium, with a bowl mouth facing up;
4) dissociating the umbilical cord mesenchymal stem cells cultured in step 1), performing resuspension uniformly, dripping an absorbed cell suspension into a concave surface of the bowl-shaped silicone hydrogel carrier, and placing the cells into an incubator for culture after the cells are settled;
5) performing periodic washing and exchange of the complete medium, performing washing after the umbilical cord mesenchymal stem cells overspread the silicone hydrogel carrier, transferring the silicone hydrogel carrier to a lenses access box filled with the complete medium, and sealing the silicone hydrogel carrier with a sealing film; and
6) irradiating the sealed bowl-shaped silicone hydrogel carrier to obtain lenses; wherein the bowl-shaped silicone hydrogel carrier is polymerized from an organosilicone monomer and a hydrophilic monomer under an action of a cross-linking agent and an initiator; the silicone monomer is polymerized from hydrogenated silicone oil and allyl methacrylate by a polymerization inhibitor and a catalyst.

11. The preparation method of the lenses for treating ocular diseases of claim 9, wherein a preparation method of the organosilicone monomer is as follows: mixing hydrogenated silicone oil, allyl methacrylate, a solvent and a polymerization inhibitor in a solvent uniformly, performing heating under inert atmosphere, adding a catalyst, performing a reaction, and performing distillation under reduced pressure after completion of the reaction to produce the silicone monomer.

12. The preparation method of the lenses for treating ocular diseases of claim 9, wherein a preparation method of the bowl-shaped silicone hydrogel carrier is as follows: mixing an organo-siloxane monomer, a hydrophilic monomer, an initiator and a cross-linking agent in a solvent to obtain a mixed solution, filling a plastic mold with the mixed solution, introducing nitrogen, performing heat curing, lathing a polymer rod obtained after curing to be of a button shape, and finally cutting the button-shaped material on two sides to produce the bowl-shaped silicone hydrogel carrier.

13. A method of the lenses of claim 1 in treatment of the chronic ocular graft-versus-host disease.

14. A method of the lenses of claim 1 in treatment of Mooren's corneal ulcer.

15. A method of the lenses of claim 1 in inhibition of post-keratoplasty rejection.

\* \* \* \* \*